United States Patent [19]

Kozlov et al.

[11] Patent Number: 5,024,658
[45] Date of Patent: Jun. 18, 1991

[54] METHOD AND DEVICE FOR THE DIAGNOSIS AND TREATMENT OF NASAL DISEASES

[76] Inventors: Vladimir S. Kozlov, Narodny pereulock, 6kv. 20; Gennady I. Markov, ulitsa Ukhtomskogo, 19, kv. 32; Vladimir P. Bugrov, ulitsa Uglicheskava,6a, kv. 43, all of, Yaroslavl, U.S.S.R.

[21] Appl. No.: 362,873

[22] Filed: Jun. 7, 1989

[30] Foreign Application Priority Data

Jun. 13, 1988 [SU] U.S.S.R. .............................. 4432024
Jun. 13, 1988 [SU] U.S.S.R. .............................. 4432025

[51] Int. Cl.$^5$ ........................................... A61M 29/00
[52] U.S. Cl. ..................................... 604/96; 604/101; 606/196
[58] Field of Search .................................. 609/96–103; 128/207–215; 606/196

[56] References Cited

U.S. PATENT DOCUMENTS 2,936,760  5/1960  Gants ................................. 604/101
3,766,924  10/1973  Pidgeon ............................ 604/101

FOREIGN PATENT DOCUMENTS 1311714  5/1987  U.S.S.R. .

Primary Examiner—Stephen C. Pellegrino
Assistant Examiner—Ralph H. Lewis
Attorney, Agent, or Firm—Burgess, Ryan & Wayne

[57] ABSTRACT

A device has an elongated body with a through longitudinally extending passage. An inflatable cuff is provided intermediate the ends of the body, and an inflatable vessel is secured to one end of the body and communicates with the passage. The cuff is mounted for movement on the body and a tube is rigidly and sealingly secured therein for receiving an instrument. An extension of the tube may be provided for carrying out the diagnosis. A method for the diagnosis and treatment of sinusitises is disclosed.

3 Claims, 1 Drawing Sheet

METHOD AND DEVICE FOR THE DIAGNOSIS AND TREATMENT OF NASAL DISEASES

FIELD OF THE ART

The invention relates to the medicine, and more specifically, it deals with otorhinolaringology, and more particularly, it relates to a method and device for the diagnosis and treatment of nasal diseases. The invention may be most advantageously used for the treatment of sinusitises.

BACKGROUND OF THE INVENTION

Widely known in the art is a method for the diagnosis of sinusitises, comprising puncturing the wall of the sinus with a needle, sampling the contents of the sinus and carrying out the analysis. Devices for the diagnosis by this method are in the form of needles of diverse configuration and size. It is necessary to puncture individually the maxillary sinus, the frontal sinus, the ethmoidal and clinoid cells, both left and right, with injuries to the osteal walls and mucuous membrane of the nasal cavity and sinuses. It will be, therefore, apparent that the methods for the diagnosis associated with puncturing are very injurious and are not very accurate at that. For this reason, special instruments have been developed for carrying out the diagnosis and treatment without puncturing.

Thus known in the art is an endoscope for the examination of the outlet openings of the accessory nasal sinuses when it is possible to examine the outlet openings of the sinuses opening into the nasal cavity and to carry out the diagnosis of sinusitis in case there is an escape of pathological contents therefrom. However, in case of incomplete filling of the sinuses with a pathological fluid and with a viscous pathological secretion, there is no evacuation of the fluid into the nasal cavity through the outlet openings so that it is not possible to carry out the diagnosis of sinusitis using the endoscope.

Also known in the art is a device comprising a tube reinforced by a plastic rod having an inflatable vessel and a cuff and three passages two of which are each connected to the vessel and cuff, respectively, and the third passage has an outlet port communicating with the tube surface at a point between the cuff and the vessel. The cuff and the vessel are rigidly secured to the flexible tube. The third passage has an adapter for connecting to a syringe (cf. SU,A, 1311714).

In using this device, the reinforced tube is inserted into the nasal cavity, the nasal cavity in seald off on the nostril and rhinopharynx sides by inflating the cuff and the vessel. Vacuum is connected to the nasal cavity sealed off in this manner so as to sample the contents of the sinuses. However, the above described device does not allow one to tell exactly from which one of the sinuses the secretion has been evacuated so that the topical diagnosis of sinusitis cannot be ensured.

SUMMARY OF THE INVENTION

It is an object of the invention to provide a device for the diagnosis and treatment of nasal diseases which ensures reliable and accurate positioning of an instrument in the nasal cavity.

Another object of the invention is to provide a method ensuring highnly accurate topical diagnosis of sinusitis.

These and other objects are accomplished by providing a device for the diagnosis and treatment of nasal diseases, comprising an elongated flexible body, an inflatable cuff provided intermediate the ends thereof, and an inflatable vessel secured to one end of the body and communicating with a through passage of the body. According to the invention, the cuff is mounted for an axial movement along the body and is provided with a tube for receiving an instrument rigidly secured thereto.

This construction allows an instrument such as an otorhinolaringofibroscope installed in the tube to be applied to the opening of a sinus being examined, and a careful examination can be carried out with the simultaneous formation of a sealed-off cavity to which vacuum may be applied. A non-puncturing topical diagnosis of sinusitises is thereby provided.

Depending on specific situation, a syringe for sampling contents of the sinuses or otorhinolaringofibroscope may be received in the tube.

For the diagnosis of sinusitises, an otorhinolaringofibroscope is inserted through the tube retained in the cuff into the sealed-off cavity to examine the openings of the sinuses so as to ensure an accurate topical diagnosis.

BRIEF DESCRIPTION OF THE DRAWINGS

The invention will now be described with reference to specific embodiments illustrated in the accompanying drawings, in which;

In the description that follows identical parts in the drawings are shown at identical reference numerals.

With reference to FIG. 1, a device for the treatment of nasal diseases and accessory nasal sinuses comprises a flexible elongated tubular body 1 made of Latex. The body 1 has a through passage 2 designed for supplying air to an inflatable vessel 3 provided at the end of the body. The body is reinforced with a rod 4, and an inflatable cuff 5 is mounted outside the body intermediate the ends thereof and communicates with a passage 6 incorporating a valve 7. There is also provided a valve 8 in the passage 2. A tube 9 is rigidly secured in the cuff 5, and points of the tube mating with the cuff are reliably sealed so as to avoid air escape from the cuff during its inflation. The tube 9 has an adapter 10 for a syringe (not shown) and a plug 11.

Figure 1:
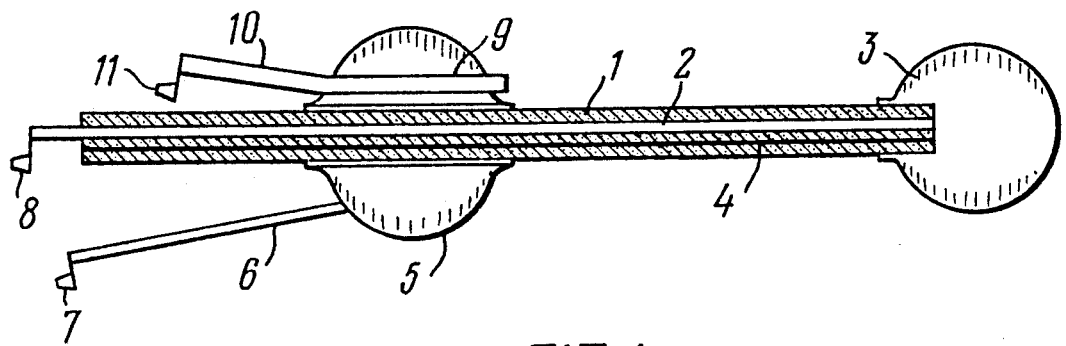
FIG. 1 shows, in a longitudinal section, a device for the treatment of sinusitises according to the invention.

The abovedescribed device may be used for the treatment of sinusitis in the following manner. After an appropriate anesthesia and anemization of the nasal cavity, it is cleaned, e.g. by blowing the nose. The body is then inserted with the end thereof carrying the inflatable vessel 3 through the inferior part of the common nasal passage so as to bring the vessel up to the choana. The cuff 5 is then positioned in the vestibule of the nose by moving it along the body 1 in accordance with individual dimensions of the common nasal passage so that the cuff be located in front of the end of the inferior turbinated bone. A syringe is inserted into the valve 8 to inflate the vessel 3 through the passage 2 so as to seal off the rhinopharynx. As a result, a sealed-off space is formed which includes the nasal cavity and the accessory nasal sinuses. Then evacuation of the contents, irrigation and introduction of medical substances are carried out using a syringe through the passage of the tube 9 and adapter 10 in the known per se manner.

Figure 2:
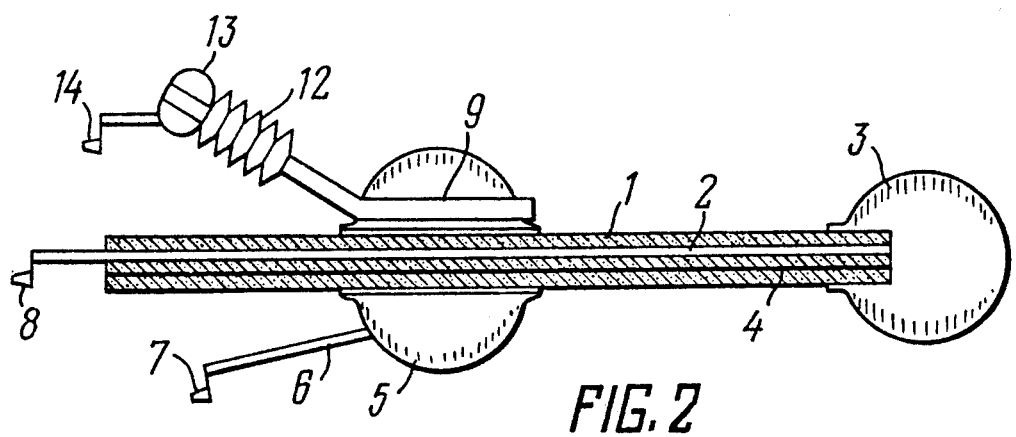
FIG. 2 is another embodiment of a device according to the invention mainly designed for the diagnosis of sinusitises.

The device shown in FIG. 2 is substantially similar to that shown in FIG. 1, with the only difference that it is provided with an extension in the form of bellows 12 terminating in a sealing member 13, e.g. in the form of a vessel containing compressed air supplied through a valve 14. This device is designed for the diagnosis of sinusitises. Operation of this device is similar to that described above, but instead of a syringe, an otorhinolaringofibroscope is introduced through the sealing member 13, bellows 12 and passage of the tube 9 after the formation of the sealed-off cavity to bring the instrument up to the sinus to be examined. Air is evacuated through a port of the otorhinolaringofibroscope to create a negative pressure in the nasal cavity. The pathological contents is thus evacuated through the natural outlet opening and can be observed through the optical system of the otorhinolaringofibroscope. The fibroscope is then positioned consecutively opposite to the openings of the rest of the sinuses in the half of the nose under examination by extending the bellows 12. Sampling of contents for analysis is carried out from the sinuses in which pathological contents have been detected is carried out through the evacuation port of the fibroscope.

The non-puncture highly-accurate topical diagnosis and treatment are thereby ensured so as to cut down examination and treatment time to a large extent.

A preferred construction of a device for the treatment and diagnosis of nasal diseases was described above, and it will be understood that modifications can be made by those skilled in the art without going beyond the spirit and scope of the invention. Thus bellows may be replaced by an extension made of an extensile material to thereby vary the extension size, and vessel with compressed air may be replaced by any other appropriate means.

We claim:

1. A device for the diagnosis and treatment of nasal diseases, comprising an elongated flexible body, a longitudinally extending through passage in said body, an inflatable cuff provided intermediate the ends of said elongated body for movement therealong, an inflatable vessel mounted at one end of said elongated body and communicating with said through passage; a tube means rigidly secured in said cuff for axial movement therewith with respect to the body and for communicating with a nasal passage to enable a medical instrument to pass therethrough, evacuate the contents of the nasal sinuses or to introduce medication into the sinuses.

2. A device according to claim 1, wherein the tube means secured in the cuff is provided with a hollow removable extension which extends axially along the body.

3. A device according to claim 2, wherein the extension comprises bellows.

* * * * *